United States Patent [19]

Uragami

[11] 4,391,270

[45] Jul. 5, 1983

[54] MAGNETIC MEDICAL TREATMENT MEMBER

[76] Inventor: Hideaki Uragami, 12-12, Mefugaoka, Takarazuka-shi, Hyogo 665, Japan

[21] Appl. No.: 237,165

[22] PCT Filed: May 28, 1980

[86] PCT No.: PCT/JP80/00115

§ 371 Date: Apr. 6, 1981

§ 102(e) Date: Feb. 17, 1981

[87] PCT Pub. No.: WO81/00357

PCT Pub. Date: Feb. 19, 1981

[30] Foreign Application Priority Data

Aug. 6, 1979 [JP] Japan .................................. 54-100519
Jan. 24, 1980 [JP] Japan .................................. 55-7860[U]

[51] Int. Cl.$^3$ ............................................. A61N 1/42
[52] U.S. Cl. ..................................................... 128/1.3
[58] Field of Search .................................... 128/1.3, 1.5

[56] References Cited

U.S. PATENT DOCUMENTS

| | | | |
|---|---|---|---|
| 3,921,620 | 11/1975 | Nakayama | 128/1.3 |
| 4,095,587 | 6/1978 | Ishikawa | 128/1.3 |
| 4,162,672 | 7/1979 | Yazaki | 128/1.3 |
| 4,197,840 | 4/1980 | Beck et al. | 128/1.3 |

FOREIGN PATENT DOCUMENTS 2235015 1/1974 Fed. Rep. of Germany ....... 128/1.3

*Primary Examiner*—William E. Kamm
*Attorney, Agent, or Firm*—Jordan and Hamburg

[57] ABSTRACT

The present invention relates to the construction of a magnetic medical treatment member comprising a flat magnetic press element mounted upon a sticking surface of a sticking member for providing simultaneously a finger-pressure effect and a magnetic medical treatment effect.

The conventional magnetic medical treatment member of this type has such a construction that a plurality of projections for locally stimulating a surface of skin are mounted on a surface of a flat magnetic press element near the central portion thereof and thus a sufficiently enough medical treatment effect can not be provided owing to the weakness of lines of magnetic force. Besides, the flat magnetic press element of this type made of magnetic materials prepared by compression molding powdery materials such as ferrite and then sintering the resulting molded products is rough to the touch and unattractive and consequently a psychological medical treatment effect can not be expected.

According to the present invention, lines of magnetic force are concentrated onto the positions of projections (4) to succeed in the improvement of a magnetic medical treatment effect by means of a magnetic medical treatment member by mounting projections (4) upon a surface of a flat magnetic press element (3) along a periphery portion thereof and forming angle portions (5), convex portions (6) and concave portions (7) on side walls of said flat magnetic press element (3) at the positions corresponding to said projections (4).

Besides, the touch and looking of said flat magnetic press (3) element are improved by forming a metal layer (9) on a surface of said flat magnetic press element (3) by means of plating process and thus also a psychological medical treatment effect can be added.

13 Claims, 11 Drawing Figures

MAGNETIC MEDICAL TREATMENT MEMBER

FIELD OF THE INVENTION

The present invention relates to a magnetic medical treatment member carrying a magnetic press element which is stuck on the surface of the skin to act as a pressing force thereof, thereby to provide a finger-pressure effect and simultaneously penetrate lines of magnetic force inwardly through the skin and thereby provide a magnetic medical treatment effect. In particular the invention relates to a magnetic medical treatment member having a plurality of projections provided upon the surface of the magnetic press element to concentrate lines of magnetic force onto the positions of each projection and simultaneously provide a psychological medical treatment effect by improving the touch and external appearance of same.

BACKGROUND OF THE INVENTION

The conventional magnetic medical treatment member of this type, as shown in FIG. 10, has such a construction that a plurality of projections (4) are provided upon a flat magnetic press element (3) near the center thereof which is mounted on a sticking surface (2) of a circular sticking member (1). Although each projection presses and stimulates acupoints and meridians and simultaneously lines of magnetic force from the flat magnetic press element (3) penetrates inwardly through the skin to provide a magnetic medical treatment effect when this magnetic medical treatment member is stuck on the surface of the skin, the magnetic medical treatment member of such a construction has the disadvantage that there is not a sufficient medical treatment effect provided because the action of the lines of magnetic force is weak.

In order to make the reasons for this clear, the inventor of the present invention observed the state of lines of magnetic force in the conventional magnetic press element to find the following phenomena:
   a. The lines of magnetic force tend to be concentrated onto projections on the flat magnetic press element.
   b. The lines of magnetic force tend to be concentrated along a periphery of the flat portion of the flat magnetic press element.
   c. The lines of magnetic force tend to be concentrated in the corner portions and convex or concave portions having a large curvature along the periphery of the flat magnetic press element.

The above described phenomena (a~c) can be deemed to be connected with the length of lines of magnetic force (magnetic resistance) and the density of spin on a surface of the flat magnetic press element and the like.

In the conventional magnetic medical treatment member as shown in said figure the degree of concentration of lines of magnetic force onto each said projection is low because each projection (4) is arranged on a surface of the flat magnetic press element (3) near the center of same and in addition, the lines of magnetic force (X) are dispersed toward the projections (4) and a peripheral portion of the flat magnetic press element (3), as shown in FIG. 11. Consequently, it can be supposed that a sufficient magnetic medical treatment effect can not be provided.

In addition, the flat magnetic press element is made of magnetic material which was obtained by compression molding of powdery materials such as ferrite and then sintering the resulting molded products, but such magnetic materials are rough to the touch and have an unattractive blackish external appearance to remarkably reduce their market value. Moreover, they are poor in a psychological medical treatment effect to which a great importance is attached in medical treatments because they are not good-looking.

An object of the present invention is to concentrate lines of magnetic force thereby to remarkably improve the magnetic medical treatment effect of a magnetic medical treatment member by devising the shape of a flat magnetic press element and the arrangement of projections, utilizing the special characteristics of the lines of magnetic force labeled paragraphs in the above described a to c.

Another object of the present invention is to provide a magnetic medical treatment member in which the market value and psychological medical treatment effect are improved by plating a surface of a flat magnetic press element with metal.

DISCLOSURE OF THE INVENTION

The present invention relates to a magnetic medical treatment member comprising a flat magnetic press element mounted upon a sticking surface of a sticking member, in which the flat magnetic press element is provided with a plurality of projections along a periphery portion of a surface thereof. Thus, the lines of magnetic force from the flat magnetic press element are concentrated onto each projection so that they may penetrate the deep portion of skin to provide a sufficient medical treatment effect by the combined action of pressure-stimulation by the projections and the lines of concentrated magnetic force.

Moreover, the magnetic medical treatment member according to the present invention is provided with angle portions on the side walls of the flat magnetic press element corresponding to each of the plural projections arranged along a periphery portion of a surface of the flat magnetic press element thereby lines of magnetic force from the flat magnetic press element are still more concentrated onto the positions of the projections to improve the magnetic medical treatment effect even more.

Moreover, the magnetic medical treatment member according to the present invention comprises a plurality of projections arranged along a periphery portion of a surface of the flat magnetic press element, depressions being formed on side walls between adjacent projections to provide convex portions and concave portions at the positions of the projections and intermediate positions between them, respectively thereby lines of magnetic force from the flat magnetic press element are still more concentrated onto the positions of the projections to improve the magnetic medical treatment effect even more like the case when angle portions are provided.

Moreover, the magnetic medical treatment member according to the present invention comprises a plurality of projections arranged along a periphery portion of a surface of the flat magnetic press element and a surface of the flat magnetic press element is plated with metals such as gold, silver, copper and the like thereby a beautiful appearance of said flat magnetic press element is provided and thus its market value is improved. Simultaneously, the psychological medical treatment effect is increased by a grave metallic luster of the flat magnetic press element.

DESCRIPTION OF THE PREFERRED EMBODIMENT

The present invention includes all magnetic medical treatment members which belong to the type in which a flat magnetic press element is stuck on a surface of the skin by means of a sticking member, for example various kinds of variations in which only one flat magnetic press element is mounted on a sticking member of small area, or a plurality of flat magnetic press elements are mounted on a sticking member such as a belt-like tape and the like.

Figure 1:
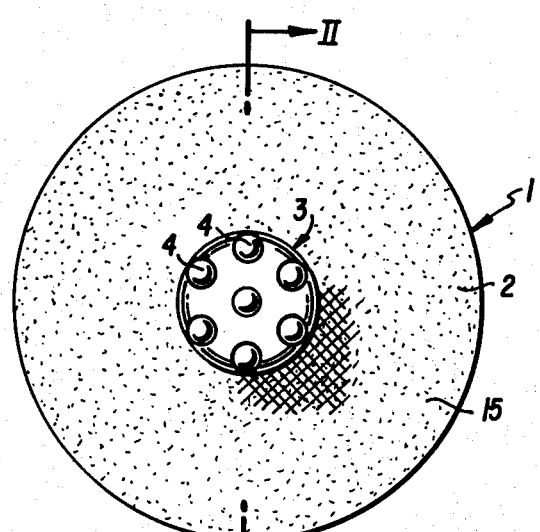
FIG. 1 is a plan view showing a magnetic medical treatment member according to the present invention.

FIG. 1 shows a preferred embodiment in which a flat circular magnetic press element (3) is mounted on a sticking surface (2) of a circular sticking member (1) of small area such as adhesive tape or the like. Magnetic members for this flat magnetic press element are obtained by compression molding powdery materials such as ferrite and then sintering the resulting molded products followed by magnetizing, the flat magnetic press element (3) being provided with a plurality of small semicircular projections (4) for locally stimulating acupoint and meridians at the central portion of its surface and along its periphery at an angular interval of 60° as a unit.

Figure 3:
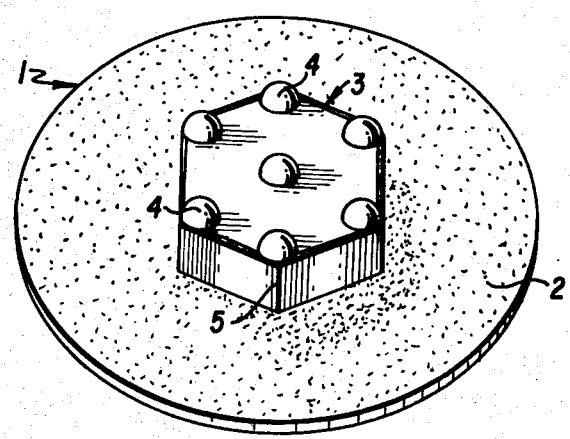
FIG. 3 is a perspective view showing another preferred embodiment of a magnetic medical treatment member according to the present invention.

FIG. 3 shows a preferred embodiment in which angle portions (5) are formed on the side walls of flat magnetic press elements (3) corresponding to the positions of the projections (4) mounted along a periphery thereof to change them from plane to hexagonal in shape. The shape of the flat magnetic press element (3) may be optional such as pentagonal, octagonal and the like by optionally increasing or decreasing the number of the projections.

Figure 4:
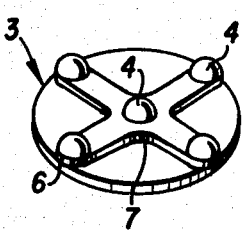
FIG. 4 and FIG. 5 are perspective views showing other preferred embodiments of a flat magnetic press element.
Figure 5:
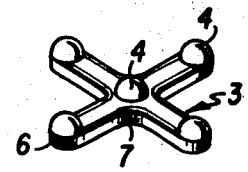

FIG. 4 and FIG. 5 show preferred embodiments in which the flat magnetic press element (3) is provided with projections (4), (4) at the central portion thereof and along its periphery at the same angular interval of 90° as a unit. Side walls of the flat magnetic press element (3) are concave between adjacent projections. The projections (4), (4) mounted along the periphery form convex portions (6) of big curvature at the positions corresponding to the positions of projections mounted on the flat magnetic press element (3) and concave portions (7) intermediately the projections, respectively. In particular, FIG. 4 shows a preferred embodiment in which the side walls of the flat magnetic press element (3) are concave only at the surface portions thereof while FIG. 5 shows a preferred embodiment in which the side walls of the flat magnetic press element (3) are collectively concave.

Figure 2:
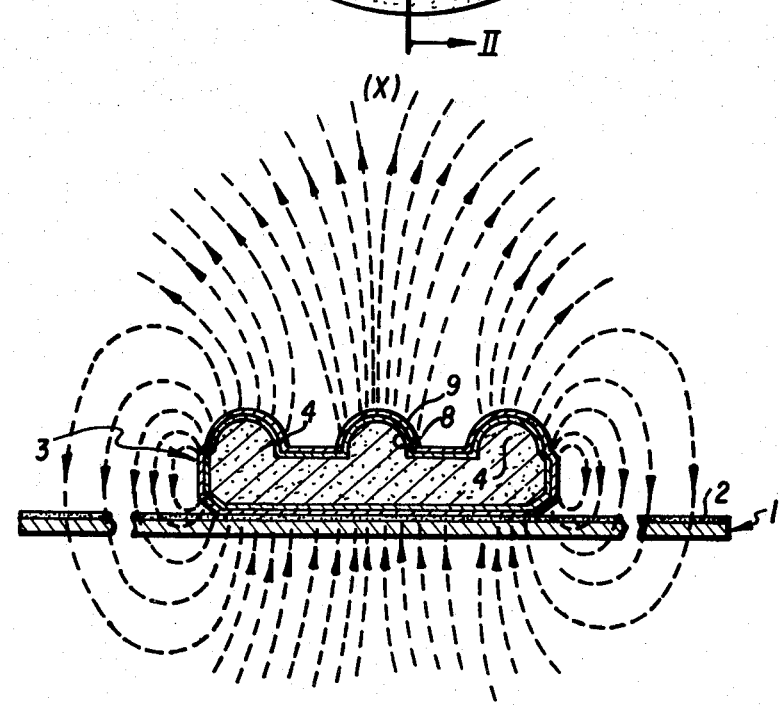
FIG. 2 is a cross-sectional view taken along the line II—II of FIG. 1 showing the state of distribution of the lines of magnetic force.

In the above described preferred embodiments, the flat magnetic press element (3) is covered with a layer of metals (9) such as gold, platinum, silver, copper and the like all over the surface thereof including the projections (4) through the intermediary of an intermediate layer (8) coated by means of cupric sulfate, as shown in FIG. 2.

Figure 7:
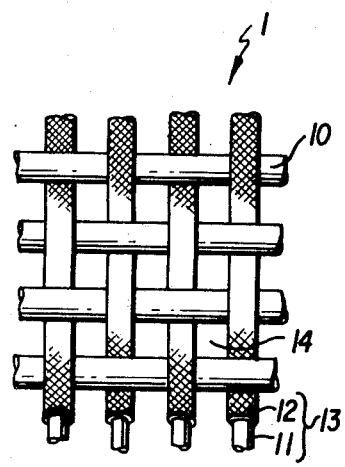
FIG. 7 is an enlarged view showing the construction of the fibers used in a sticking member.

Furthermore, a sticking member (1), as shown in FIG. 7, is made of a flexible sheet material provided with spaces (14) for passing air between flexible woofs (10) made of cotton, staple fiber and the like and flexible warps (13) which are prepared by covering elastic yarns (11) such as rubber yarns and the like with fibers (12) such as cotton, staple fiber and the like and weaved alternately to and in a right-angled relation to the flexible woofs (10).

In addition, an adhesive layer (2) of the sticking member (1) may include powdery silver or copper (15) having a sterilizing effect.

INDUSTRIAL UTILITY VALUE

Figure 6:
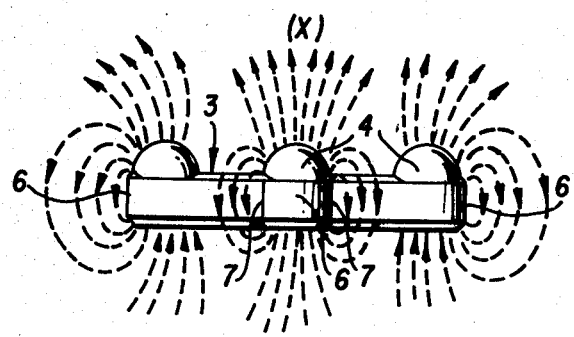
FIG. 6 is a front view showing the state of distribution of the lines of magnetic force around the flat magnetic press element shown in FIG. 5.
Figure 8:
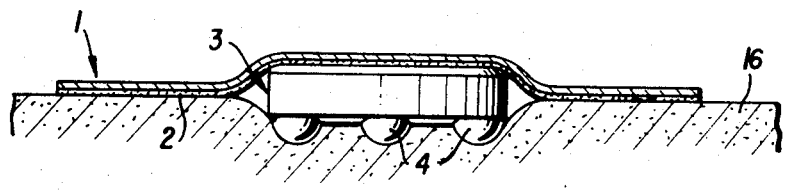
FIG. 8 and FIG. 9 show the state of the magnetic medical treatment member shown in FIG. 1 which is stuck on the skin.
Figure 9:
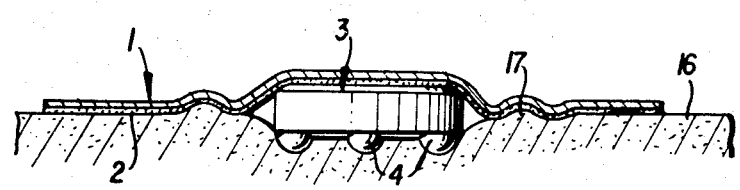
Figure 10:
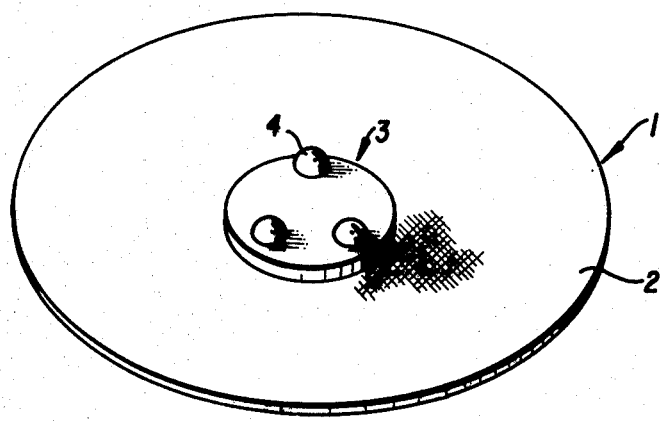
FIG. 10 is a perspective view showing a conventional magnetic medical treatment member.
Figure 11:
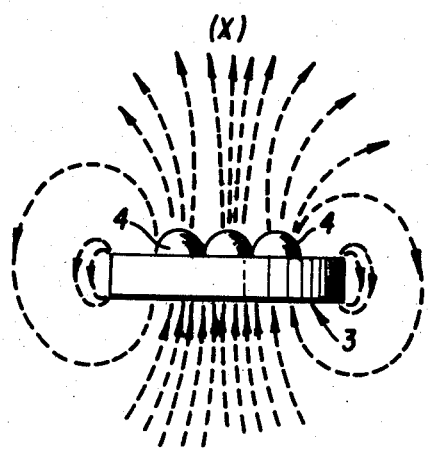
FIG. 11 is a front view showing the state of distribution of the lines of magnetic force around the conventional flat magnetic press element shown in FIG. 10.

When the magnetic medical treatment member according to the present invention is stuck on a surface of the skin (16) (see FIG. 8), the surface of skin (16) receives a pressing force from the flat magnetic press element (3), in particular the local stimulation by each projection (4) can provide an effective finger-pressure effect. Simultaneously, lines of magnetic force act from the flat magnetic press element (3) onto the skin (16). However, lines of magnetic force tend to concentrate on the projections of the flat magnetic press element (3) rather than its flat portion and along its periphery rather than the central portion of its surface, respectively. Referring now to FIG. 1 and FIG. 3 to 5, the projections (4) are arranged along a periphery of a surface of the flat magnetic press element (3) and thus lines of magnetic force (X) are concentrated on the positions of the projections (4) owing to the combined effect of the above described phenomena (see FIG. 2) to act on the affected part and consequently, a sufficient medical treatment effect can be provided from the pressing stimulation effect by the projections (4) and the action of the lines of magnetic force. Besides, the lines of magnetic force tend to concentrate on the angle portions and the concave and convex portions of big curvature along a periphery of the flat magnetic press element (3), that is to say, in the preferred embodiments shown in FIGS. 3 to 5, the lines of magnetic force tend to concentrate still more on the positions of the angle portions (5) and the convex portions (6) at which the projections (4) are located along a periphery of the flat magnetic press element (3), in particular, in the preferred embodiments shown in FIGS. 4 and 5, lines of magnetic force (X) are concentrated also on the concave portions (7) adjacent to the central projection (4) and thus the lines of magnetic force (X) are concentratedly on the affected part (see FIG. 6).

Besides, a smooth surface of a metal layer obtained by plating (9) provides an agreeable touch to the skin (16), and a grave and beautiful metallic luster of the metal layer (9) increases the psychological medical treatment effect. Thus, the combination of a finger-pressure effect and the magnetic medical treatment effect with a psychological medical treatment leads to an increased medical treatment effect. In particular, when the metal layer (9) comprises gold, the ionization of gold is accelerated by a substances such as ammonia, uric acid and the like oozed out from the body onto a surface of the skin (16) and the resulting gold ions exhibit their effect to medical treatment of articular rheumatism. Besides, when the metal layer (9) comprises silver or copper, an ionization of silver or copper is accerelated by the above described substances oozed out from the body onto a surface of the skin (16) and the resulting silver ions or copper ions may prevent rash from occurring owing to their sterilizing effect.

Furthermore, when the sticking member (1) is made of flexible sheet materials, as shown in the preferred embodiments of the present invention, the sticking member (1) is difficult to tear off from the skin (16) because the sticking member (1) expands and contracts in accordance with the expansion and contraction of the muscles and the generation of wrinkles. Besides, when the sticking member (1) is expanded, a contracting force of the sticking member (1) acts on the flat magnetic press element (3) as a pressing force against the skin (16) to strengthen still more the pressing stimulation.

What is claimed is:

1. A magnetic treatment member comprising a generally flat magnetic press element mounted on a sticking surface of a sticking member, said magnetic press element having a generally flat surface extending to an outer peripheral edge of said magnetic press element, said magnetic press element having an outer peripheral wall along said outer peripheral edge, and a plurality of projections protruding from said flat surface, said projections extending substantially to said outer peripheral edge such that said projections are substantially continuous with said outer peripheral wall, whereby the lines of magnetic force are concentrated on said projections.

2. A magnetic treatment member according to claim 1 wherein said projections are substantially contiguous with said outer edge, and said lines of magnetic force are concentrated about said projections without being dispersed by any substantial flat wall surface between said projections and said outer wall.

3. A magnetic treatment member according to claim 1 wherein said magnetic press element has a substantially polygonal configuration having a plurality of angled peripheral edges, said projections being disposed at said angled peripheral edges, whereby the magnetic lines of force are concentrated on said projections at said angled peripheral edges.

4. A magnetic treatment member according to claim 1 wherein said magnetic press element has a plurality of generally radially extending arm elements, said projections being disposed at the radial outer ends of said arm elements, whereby the magnetic lines of force are concentrated on said projections at the radial outer ends of said arm elements.

5. A magnetic treatment member according to claim 4 wherein said radially extending arm elements define generally concave spaces therebetween.

6. A magnetic treatment member according to claim 4 wherein said arm elements have a width substantially equal to the diameter of said projections.

7. A magnetic treatment member according to claim 4 wherein said arm elements have an outer peripheral wall with the portion of the outer peripheral wall disposed at the outer radial end of said arm elements having a convex configuration.

8. A magnetic treatment member according to claim 4 further comprising a projection disposed at the central portion of said magnetic press element.

9. A magnetic treatment member according to claim 4 wherein said magnetic press element further comprises a generally flat member on which said arm elements are disposed.

10. A magnetic treatment member according to claim 9 wherein said arm elements have an outer wall, and said generally flat member has an outer wall which is continuous with portions of said outer wall of said arm elements.

11. A magnetic treatment member according to claim 1 wherein said sticking member is made of a flexible sheet material.

12. A magnetic treatment member according to claim 1 wherein said magnetic press element has a metal plating thereon.

13. A magnetic treatment member according to claim 12 wherein said metal plating is gold.

* * * * *